United States Patent [19]

Moreland et al.

[11] Patent Number: 4,745,180

[45] Date of Patent: May 17, 1988

[54] SOLUBILIZATION OF PROTEINS FOR PHARMACEUTICAL COMPOSITIONS USING HEPARIN FRAGMENTS

[75] Inventors: Margaret Moreland; Danute E. Nitecki, both of Berkeley, Calif.

[73] Assignee: Cetus Corporation, Emeryville, Calif.

[21] Appl. No.: 879,456

[22] Filed: Jun. 27, 1986

[51] Int. Cl.$^4$ .................... C07K 15/00; A61K 45/02; A61K 37/02; A61K 39/00

[52] U.S. Cl. .................................. 530/351; 530/395; 530/389; 530/390; 530/391; 530/402; 530/403; 530/405; 514/2; 514/8; 514/56; 424/85; 435/811

[58] Field of Search .................. 514/2, 8, 56; 424/85–87; 530/351, 402, 403, 405, 395, 389–391; 435/811

[56] References Cited

U.S. PATENT DOCUMENTS

| | | |
|---|---|---|
| 3,619,371 | 11/1971 | Crook et al. . |
| 4,055,635 | 10/1977 | Green et al. . |
| 4,496,689 | 1/1985 | Mitra .................................. 514/59 |
| 4,518,584 | 5/1985 | Mark et al. ......................... 530/351 |
| 4,588,585 | 5/1986 | Mark et al. ......................... 530/351 |
| 4,613,665 | 9/1986 | Larm ................................. 525/34.2 |

FOREIGN PATENT DOCUMENTS

| | | |
|---|---|---|
| 0154316 | 9/1985 | European Pat. Off. . |
| 0147761 | 7/1985 | European Pat. Off. . |
| 8603318 | 3/1985 | PCT Int'l Appl. . |
| 8700056 | 1/1987 | PCT Int'l Appl. . |

OTHER PUBLICATIONS

Kim et al., CA, vol 102, 1985, #219467r.
Function of Proteoglycans, ed. Evered et al., 1986, pages vary.
Kim et al., *Korean Biochem. J.*, 1985, vol. 18(1), pp. 50–55.
Hoffman et al., *Carbohydrate Research*, 117, 328–331, (1983).
Hoylaerts et al., *Thromb. Haemostas* (Stuttgart) 49:109 (1983).
Ceustermans et al., *J. Biol. Chem.*, 257:3401 (1982).
Bjork et al., *FEBS Letters*, 143(a), 96 (1982).

*Primary Examiner*—Morton Foelak
*Assistant Examiner*—Garnette D. Draper
*Attorney, Agent, or Firm*—Janet E. Hasak; Albert P. Halluin

[57] ABSTRACT

A pharmaceutical composition is prepared wherein a biologically active conjugated protein which is β-interferon, interleukin-2, or an immunotoxin is dissolved in an aqueous carrier medium without the presence of a solubilizing agent. The unconjugated protein, which is poorly or not at all water-soluble at pH 6–8 without such solubilizing agent, is selectively conjugated to at least one heparin fragment having a terminal 2,5-anhydro-D-mannose residue which has an aldehyde not involved in intramolecular hemiacetal formation.

16 Claims, No Drawings

SOLUBILIZATION OF PROTEINS FOR PHARMACEUTICAL COMPOSITIONS USING HEPARIN FRAGMENTS

BACKGROUND OF THE INVENTION

This invention relates to a chemical modification of biologically active proteins which alters the chemical and/or physiological properties of these proteins. More specifically, this invention relates to selective conjugation of lipophilic poorly watersoluble proteins to heparin fragments to render the proteins more soluble at physiological pH.

Many heterologous proteins produced in microbial host cells are found as poorly soluble or insoluble material in refractile bodies. Examples of heterologous proteins which form refractile bodies in commonly found culture conditions include interleukin-2 (IL-2), interferon-$\beta$ (IFN-$\beta$), feline leukemia virus (FeLV) envelope protein, human growth hormone (hGH), bovine growth hormone (bGH), porcine growth hormone (pGH), and certain proteins coated or fused with a virus such as FMD virus. Many of these proteins are hydrophobic in nature and tend to stick to materials and to themselves (i.e., aggregate) rather than remain in solution. Also, many of these recombinant proteins are unglycosylated, whereas their native counterparts are glycosylated water-soluble molecules. Modifications of these proteins which might alter their solubility properties would be desirable to increase production yields as well as to facilitate their formulation for therapeutic use. In addition, modifications may reduce or eliminate aggregation of the protein when it is introduced in vivo, thereby reducing its immunogenicity.

The use of polypeptides for the purpose of producing a particular physiological response is well known in the medicinal arts. A limitation to the potential therapeutic benefit derived from the clinical use of polypeptides is their ability to elicit an immune response. This immune response may be caused or aggravated by aggregates in the material prior to injection as described by R. Illig (1970), *J. Clin. Endrocr.*, 31, 679–688, W. Moore (1978), *J. Clin. Endrocrinol. Metab.*, 46, 20–27 and W. Moore and P. Leppert (1980), *J. Clin. Endrocrinol. Metab.*, 51, 691–697. This response involves the production of antibodies to the polypeptides. This antibody production may decrease or eliminate the desired biological function of the polypeptide, sometimes by causing reduced residence time in the circulatory system (reduced half-life) or by modifying the molecule by virtue of the antibody-polypeptide interaction.

Modification of these potentially useful therapeutic polypeptides so as to preclude or at least reduce an immune response while still maintaining desired physiological a ctivities of the polypeptide would allow the use of these polypeptides in the mammalian circulatory system without the aforementioned disadvantages. In addition, due to the increased half-life of the circulating polypeptide, smaller amounts of the polypeptide would be required for the desired therapeutic effect than have heretofore been possible.

The problems of immunogenicity and short half-life in circulation set forth hereinabove and other undesirable properties of certain proteins are well recognized and various modifications of polypeptides have been undertaken to solve them. These include the modification of proteins with substantially straight chain polymers such as polyethylene glycol (PEG).

For example, U.S. Pat. No. 4,261,973 describes conjugation of immunogenic allergen molecules with non-immunogenic water-soluble polymers such as PEG to reduce the immunogenicity of the allergen.

U.S. Pat. No. 4,055,635 discloses pharmaceutical compositions comprising a water-soluble complex of a proteolytic enzyme linked covalently to a polymeric substance such as polysaccharides.

U.S. Pat. No. 4,088,538 discloses a reversibly soluble enzymatically active polymer enzyme product comprising an enzyme covalently bonded to an organic polymer such as polyethylene glycol.

U.S. Pat. No. 4,415,665 discloses a method of conjugating an organic ligand containing at least one primary or secondary amino group, at least one thiol group and/or at least one aromatic hydroxyl group (described in col. 3, lines 19–36) to a polymeric carrier with at least one hydroxyl group (described in col. 2, lines 42–66).

U.S. Pat. No. 4,496,689 discloses a covalently attached complex of alpha-1-proteinase inhibitor with a polymer such as PEG or methoxypolyethylene glycols.

U.S. Pat. No. 3,619,371 discloses a polymeric matrix having a biologically active substance chemically bound thereto.

U.S. Pat. No. 3,788,948 discloses use of organic cyanate compounds to bind proteins to polymers.

U.S. Pat. No. 3,876,501 discloses activation of water-soluble carbohydrates with cyanogen bromide to improve their binding to enzymes and other proteins.

U.S. Pat. 4,055,635 discloses pharmaceutical compositions of a proteolytic enzyme linked covalently to a polymeric substance.

JP No. 5792435 published Nov. 26, 1982 discloses modified polypeptides where all or part of the amino groups are substituted with a polyethoxyl moiety. DE No. 2312615 published Sept. 27, 1973 discloses conjugating of polymers to compounds containing hydroxyl or amino groups.

EP No. 147,761 discloses a covalent conjugate of alpha-1-proteinase inhibitor and water-soluble polymer, where the polymer may be polyethylene glycol.

EP No. 154,316, published Sept. 11, 1985 to Takeda Chemical Industries, Ltd., discloses and claims chemically modified lymphokines such as IL-2 containing PEG bonded directly to at least one primary amino group of a lymphokine.

U.S. Pat. No. 4,414,147 describes rendering interferon less hydrophobic by conjugating it to an anhydride of a dicarboxylic acid such as poly(ethylene succinic anhydride).

Copending U.S. Ser. No. 749,955 filed June 26, 1985 discloses conjugation of PEG to such proteins as interferon-$\beta$, interleukin-2 and immunotoxins.

The heparin molecule consists of (1→4)-linked 2-amino-2-deoxy-$\alpha$-D-glucopyranosyl, $\alpha$-L-idopyranosyluronic acid and a relatively small amount of $\beta$-D-glucopyranosyluronic acid residues.

Heparin has been bound covalently to solid supports to prepare blood-compatible surfaces. For example, PCT application WO86/03318 published Dec. 27, 1985 (Cardiol. Sci. Center) discloses immobilization of urokinase on a heparin support to produce a water-soluble complex with increased throbolytic activity. The conjugation is via a carboxyl group, not an aldehyde group.

It is desirable to conjugate the protein to a smaller heparin fragment. Hoffman et al., *Carbohydrate Re-*

*search,* 117, 328–331 (1983) discloses a method for producing heparin fragments using nitrous acid, wherein the fragments have 2,5-anhydro-D-mannose residues as reducing terminal units with aldehyde groups. Such aldehyde groups may be reacted with primary amines to give labile Schiff-bases which can be converted to stable secondary amines by reductive amination. Hoffman et al. describes coupling of such heparin fragments to sepharose and curdlan and suggests coupling of heparin to human serum albumin and antithrombin.

None of the references, however, disclose how to use heparin fragments to water-solubilize recombinant proteins such as IL-2 and IFN-$\beta$ which are hydrophobic and therefore resist formulation in an aqueous medium at physiological pH. Furthermore, it is not a priori possible to predict which selected proteins would be favorably responsive, e.g., have good biological activity, to treatment with heparin fragments, due to the vast difference in physical properties between enzymes or albumins, on the one hand, and cytotoxins and lymphokines, on the other hand.

SUMMARY OF THE INVENTION

Accordingly, the present invention provides for modifying those proteins selected from $\beta$-interferon, interleukin-2, and immunotoxins which are not ordinarily soluble in water under ambient conditions at pharmaceutically acceptable pH ranges to render them more soluble in aqueous buffer under such conditions. This modification may be mimicking glycosylation of the protein, thereby surprisingly rendering the protein more soluble, just as the native glycosylated protein is soluble. This modification also avoids addition of extraneous solubilizing additives such as detergents or denaturants to keep the protein in solution. The modified protein retains the biological activity of the unmodified protein, both initially and over time.

As secondary advantages, the modification under some conditions is expected to increase the physiological half-life of the protein and may decrease its immunogenicity by reducing or eliminating aggregation of the protein or by masking antigenic determinants.

More specifically, the present invention is directed to a pharmaceutical composition comprising a non-toxic, inert, pharmaceutically acceptable aqueous carrier medium in which is dissolved a biologically active selectively conjugated protein selected from the group consisting of $\beta$-interferon, interleukin-2, and an immunotoxin, wherein the protein is covalently conjugated via at least one of its lysine residues to at least one heparin fragment having a terminal 2,5-anhydro-D-mannose residue through the aldehyde group of such residue, wherein said protein in its unconjugated form is normally hydrophobic and poorly soluble in said aqueous carrier medium at pH 6–8 in the absence of a solubilizing agent.

Preferably the protein is recombinant interleukin-2.

Another aspect of this invention residues in a process for preparing a pharmaceutical composition comprising:

(a) preparing a heparin fragment polymer having a terminal 2,5-anhydro-D-mannose residue with an aldehyde not involved in intramolecular hemiacetal formation;

(b) reacting a biologically active normally hydrophobic, poorly water-soluble protein selected from the group consisting of $\beta$-interferon, interleukin-2, and an immunotoxin with said aldehyde of said heparin fragment so as to provide a more water-soluble, biologically active, selectively conjugated protein; and (c) formulating said protein in a non-toxic, inert, pharmaceutically acceptable aqueous carrier medium.

DESCRIPTION OF THE PREFERRED EMBODIMENTS

As used herein, the term "normally hydrophobic, poorly water-soluble" as describing the proteins refers to those proteins which are insoluble or not readily soluble in water or an aqueous medium under ambient conditions of room temperature and atmospheric pressure at a pH of between about 6 and 8, i.e, at about neutral or physiological pH. The modification herein acts to increase the solubility of such proteins when they are subjected to such physiological conditions. For purposes herein, solubility may be tested by (1) turbidity, as measured by spectrophotometric means, (2) S value, as measured by ultracentrifugation, wherein the monomeric protein sedimentation rate rather than the much greater aggregate sedimentation rate signals solubility, and (3) apparent native molecular weight, as measured by size exclusion chromatography. The exact numbers which would indicate solubility for each of these tests will depend on the type of buffer in which the protein is formulated, the pH of the buffer, and the inoic strength of the buffer, and various pharmacologically accepted additives.

The interferon-$\beta$ and interleukin-2 herein may be obtained from tissue cultures or by recombinant techniques, and from any mammalian source such as, e.g., mouse, rat, rabbit, primate, pig, and human. Preferably such proteins are derived from a human source, and more preferably are recombinant, human proteins.

The term "recombinant $\beta$-interferon," designated as IFN-$\beta$, preferably human IFN-$\beta$, refers to fibroblast interferon having comparable biological activity to native IFN-$\beta$ prepared by recombinant DNA techniques as described in the art. In general, the gene coding for interferon is excised from a native source and inserted into a cloning vector to be cloned and then into an expression vector, which is used to transform a host organism, preferably a microorganism, and most preferably *E. coli.* The host organism expresses the foreign interferon gene under certain conditions to produce IFN-$\beta$. More preferably, the IFN-$\beta$ is a mutein as described in U.S. Pat. No. 4,588,585, in which the cysteine normally occurring at position 17 of the wild-type or native molecule has been replaced by a neutral amino acid such as serine or alanine. Most preferably, the IFN-$\beta$ mutein is IFN-$\beta_{ser17}$.

The term "recombinant interleukin-2," designated as IL-2, preferably human IL-2, refers to interleukin-2 having comparable biological activity to native IL-2 prepared by recombinant DNA techniques as described, e.g., by Taniguchi et al., *Nature,* 302:305–310 (1983) and Devos, *Nucleic Acids Research,* 11:4307–4323 (1983). In general, the gene coding for IL-2 is excised from a native source and inserted into a cloning vector to be cloned and then into an expression vector, which is used to transform a host organism, preferably a microorganism, and most preferably *E. coli.* The host organism expresses the foreign gene to produce IL-2 under expression conditions.

More preferably, the IL-2 is a mutein as described in U.S. Pat. No. 4,518,584, in which the cysteine normally occuring at position 125 of the wild-type or native molecule has been replaced by a neutral amino acid such as serine or alanine. Alternatively or conjunctively, the IL-2 mutein may be one as described in copending U.S. Application Ser. No. 810,656 filed Dec. 17, 1985, the disclosure of which is incorporated herein by reference, in which the methionine normally occurring at position 104 of the wild-type or native molecule has been replaced by a neutral amino acid such as alanine.

Preferably, the IL-2 is a protein produced by a microorganism or by yeast which has been transformed with the human cDNA sequence of IL-2 which encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (deletions, additions, substitutions) which do not cause an adverse functional dissimilarity between the synthetic protein and native human IL-2. Examples of IL-2 proteins with such properties include those described by Taniguchi et al., supra; Devos, supra; European Patent Publication Nos. 91,539 and 88,195; U.S. Pat. No. 4,518,584, supra, and copending U.S. Application Ser. No. 810,656 filed Dec. 17, 1985, supra. Most preferably, the IL-2 is $ser_{125}IL$-2, $des$-$ala_1ser_{125}IL$-2, $des$-$ala_1IL$-2, $des$-$ala_1ala_{104}IL$-2, or $des$-$ala_1ala_{104}ser_{125}IL$-2, where "$des$-$ala_1$" indicates that the N-terminal alanyl residue of the IL-2 has been deleted.

The precise chemical structure of the proteins herein will depend on a number of factors. As ionizable amino and carboxyl groups are present in the molecule, a particular protein may be obtained as an acidic or basic salt, or in neutral form. All such preparations which retain their bioactivity when placed in suitable environmental conditions are included in the definition of proteins herein. Further, the protein molecule may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the bioactivity of the protein is not destroyed. It is expected, of course, that such modifications may quantitatively or qualitatively affect the bioactivity by either enhancing or diminishing the activity of the protein in the various assays.

Often the hydrophobic recombinant proteins such as IL-2 and IFN-$\beta$ produced from transformed host cells containing recombinant DNA precipitate inside the cell as opposed to being soluble in the cell culture medium. The intracellularly produced protein must be separated from the cellular debris and recovered from the cell before it can be formulated into a purified biologically active material. Commonly owned copending U.S. Application Ser. No. 843,997 filed on Mar. 25, 1986, entitled "Process for Recovering Refractile Bodies Containing Heterologous Proteins From Microbial Hosts" to W. Hanisch et al., the entire disclosure of which is incorporated herein by reference, discloses a process for isolating such a refractile material. In this process the cell membrane of the transformed host microorganism is disrupted, greater than 99% by weight of the salts is removed from the disruptate, the desalted disruptate is redisrupted, a material, preferably a sugar such as sucrose, is added to the disruptate to create a density or viscosity gradient in the liquid within the disruptate, and the refractile material is separated from the cellular debris by high-speed centrifugation, i.e., at about 10,000 to 40,000 $\times$ g. Preferably, the salts are removed from the disruptate by diafiltration or centrifugation and sucrose is added to increase the density of the liquid to about 1.1 to 1.3 g/ml.

After the centrifugation step, the pellet containing the refractile bodies is solubilized with a denaturant such as sodium dodecyl sulfate, the resulting suspension is centrifuged, and the supernatant containing the protein is treated to isolate the protein. The protein is separated from the supernatant by appropriate means such as reverse-phase high pressure liquid chromatography (RP-HPLC) and/or gel filtration chromatography. After such separation, the protein is preferably oxidized to ensure the production of high yields of recombinant protein in a configuration most like its native counterpart. Such oxidation is described in U.S. Pat. No. 4,530,787 to Z. Shaked et al., the disclosure of which is incorporated herein by reference. The oxidation may also be carried out by reacting an aqueous solution containing a solubilized form of the protein at a pH between about 5.5 and 9 in the presence of air with at least an effective amount of an oxidation promoter containing a $Cu^{+2}$ cation, as described in U.S. Pat. No. 4,572,798 to K. Koths et al., the disclosure of which is incorporated herein by reference. The preferred oxidation promoter is $CuCl_2$ or (o-phenanthroline)$_2$ $Cu^{+2}$. After oxidation, the protein may optionally be desalted and purified further by RP-HPLC, dilution/diafiltration, S-200 gel filtration chromatography, and ultrafiltration techniques before modification with activated polymer as described further hereinbelow. The polymer modification may, however, be carried out at any step after the heterologous proetin has been isolated in sufficiently pure form to be biologically active for therapeutic purposes. The point at which the modification will occur will depend on the ultimate purity of the protein required for the final pharmaceutical formulation and use.

The term "immunotoxin" as used herein to apply to the third class of proteins refers to a conjugate of an antibody and a cytotoxic moiety. The cytotoxic moiety of the immunotoxin includes a cytotoxic drug or an enzymatically active toxin of bacterial or plant origin or an enzymatically active fragment ("A chain") of such a toxin. Examples of enzymatically active toxins and fragments thereof include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, gelonin, mitogellin, restrictocin, phenomycin, and enomycin. Ricin A chain, nonbinding active fragments of diphtheria toxin, abrin A chain, and PAPII are preferred. Most preferred is the ricin A chain, which is modified by reaction with the polymer.

The antibodies employed in the immunotoxin are preferably monoclonal antibodies directed against a specific pathological condition such as, e.g., cancers such as breast, prostate, colon or ovarian cancer, melanoma, myeloma, etc.

Conjugates of the antibody and cytotoxic moiety may be made using a variety of bifunctional protein crosslinking reagents. Examples of such reagents include N-succinimidyl-3-(2-pyridyldithio) propionate (SPDP), iminothiolane (IT), bifunctional derivatives of imidoesters such as dimethyl adipimidate . HCl, active esters such as disuccinimidyl suberate, aldehydes such as glutaraldehyde, bis-azido compounds such as bis (p-azidobenzoyl) hexanediamine, bis-diazonium derivatives such as bis-(p-diazonium-benzoyl)-ethylenediamine, diisocyanates such as tolylene-2,6-diisocyanate, and bis-active fluorine compounds such as 1,5-difluoro-2,4-dinitrobenzene.

The term "selectively conjugated" as used herein to apply to the protein refers to proteins which are covalently bonded via one or more of the lysine residues of the protein. The number of lysine residues to which the heparin fragment is bound depends mainly on the reaction conditions, the ultimate use, and the particular protein employed. The lysine is generally linked to the heparin fragment(s) through the free $\epsilon$-amino group of the lysine.

According to the process of this invention, the three types of proteins described above, which are normally hydrophobic and poorly water-soluble, are rendered soluble in an aqueous carrier medium, preferably at a pH of about 5 to 8, more preferably about 6-8 and most preferably, 6.5-7.8, without use of solubilizing agents, by modifying the proteins through conjugation to the reactive aldehyde group of a heparin fragment. The pH of the reaction is preferably about 6 to 8, more preferably 7-7.5. The success of such a modification of these proteins cannot be predicted from earlier use of heparin modification of enzymes or other proteins.

The heparin fragment to which the protein is attached has a wide range of molecular weights generally between about 10,000 and 20,000, with an average of about 16,000. In addition, the heparin fragment contains a 2,5-anhydro-D-mannose residue as the reducing terminal unit. The unit has an aldehyde group which is not involved in intramolecular hemiacetal formation.

The chemistry of the reaction between the lysine(s) of the protein and the aldehyde(s) of the heparin fragment involves formation of labile Schiff bases which convert into stable secondary amines under reducing conditions. Therefore, if the aldehyde groups are present as cyclic hemiacetals, the Schiff base does not form as readily, thereby reducing yields. As a result, the heparin fragment herein must have terminal units with aldehydes which do not form cyclic hemiacetals.

The heparin fragments are produced by partially depolymerizing heparin by deaminative cleavage to produce terminal aldehyde groups as defined above. Any oxidizing reagent which effects such deamination may be employed, such as, e.g., nitrous acid, which is preferred. Nitrous acid may be prepared by adding sodium nitrite solution to the heparin in acid (e.g., HCl, acetic acid). The depolymerization preferably takes place at room temperature for one to three hours.

Once the fragmentation has occurred, the fragments of low molecular weight are separated from the reaction mixture, as by using dialysis. The dialyzed fragments are then reacted with the protein, preferably at 37° C. and preferably for 10-30 hours, depending, for example, on the protein, in an aqueous solution, preferably at a pH of about 6-8. A reducing agent may be present in the reaction vessel or may be added after the heparin is conjugated to the protein. If the reducing agent is present at the same time, it must not adversely affect the reaction and is preferably sodium cyanoborohydride. If the reducing agent is added afterward, it may be any reducing agent which will reduce the Schiff base without damaging the protein, e.g., sodium borohydride.

After the reaction, the reaction mixture is treated to separate its components, as by transferring to a size exclusion column. The column is washed appropriately, using a buffer. The fractions from the column corresponding to the conjugates are identified by molecular weight and the protein may be identified by ultraviolet analysis. The protein is tested for water-solubility and biological activity. Preferably, at least about 10%, more preferably 25%, more preferably 50%, and most preferably 100% of the biological activity of the protein is retained.

The protein thus modified is then formulated in a non-toxic, inert, pharmaceutically acceptable aqueous carrier medium, preferably at a pH of about 3 to 8, more preferably 6-8. For in vitro applications, as for immunotoxins used for therapeutic purposes, the modes of administration and formulation are not critical. Aqueous formulations compatible with the culture or perfusion medium will generally be used. When used in vivo for therapy, the sterile product will consist of a mixture of protein dissolved in an aqueous buffer in an amount which will provide a pharmaceutically acceptable pH when the mixture is reconstituted. A water-soluble carrier such as mannitol may optionally be added to the medium. The currently formulated unmodified IL-2 is stable for at least six months at 4° C..

The dosage level of protein in the formulation will depend on the in vivo efficacy data obtained after preclinical testing and will depend mainly on the protein employed and ultimate use.

If the formulation is lyophilized, the lyophilized mixture may be reconstituted by injecting into the vial a conventional parenteral aqueous injection such as, e.g., distilled water.

The reconstituted formulation prepared as described above is suitable for parenteral administration to humans or other mammals in therapeutically effective amounts (i.e., amounts which eliminate or reduce the patient's pathological condition) to provide therapy thereto, the type of therapy being dependent on the type of protein. For example, IL-2 therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell mediated anti-tumor activity.

In an alternative to direct administration of IL-2, the IL-2 may be administered in an adoptive immunotherapy method, together with isolated, lymphokine-activated lymphocytes, in a pharmaceutically acceptable carrier, where the lymphocytes are reactive to tumor when administered with the IL-2 to humans suffering from the tumor. This method is described more fully in U.S. Pat. No. 4,690,915 issued Sept. 1, 1987 (NTIS), the disclosure of which is incorporated herein by reference, and by S. Rosenberg et al., *New England Journal of Medicine* (1985), 313:1485–1492.

IFN-$\beta$ therapy is appropriate for anti-cancer, anti-viral and anti-psoriasis treatment. Specific cancers against which IFN-$\beta$ has shown some efficacy include lymphoma, myeloma, hairy-cell leukemia and some viral diseases including veneral warts and rhinoviruses.

Immunotoxin therapy is appropriate for diseases against which the targeted antibody is effective, usually cancer. In particular, immunotoxins are being targeted for such cancers as breast cancer.

The dose and dosage regimen of the immunotoxin will depend, for example, upon the pharmacokinetics of the drug, the nature of the cancer (primary or metastic) and its population, the number and length of the heparin fragments, the characteristics of the particular immunotoxin, e.g., its therapeutic index, the patient, and the patient's history. The dose and dosage regimen of the IL-2 and IFN-$\beta$ will similarly depend, for example, on the pharmacokinetics of the drug, the nature of the disease, the characteristics of the IL-2 or IFN-$\beta$, the patient and the patient's history. For example, different modified IL-2 proteins are expected to have different pharmacokinetic and therapeutic properties which are advantageous for different routes of administration. A long-acting drug might only be administered every 3–4 days, every week or once every two weeks. It is anticipated that the clearance rate might be varied to give ultimate flexibility to fit the particular need of the patient by changing, e.g., the size of the heparin fragment attached.

In the following examples, which illustrate the invention further, all parts and percentages are by weight unless otherwise noted, and all temperatures are in degrees Celsius.

EXAMPLE I

Preparation of Heparinized Interleukin-2 (IL-2)

A. Preparation of Heparin Fragments.

To a total of 0.76 g of commercially obtained heparin in 40 ml water was added 0.1M HCl until the pH was 2.5. A solution of 6 mg of sodium nitrite in 1.0 ml water was added dropwise to the heparin solution, and the reaction mixture was stirred at room temperature for two hours. After this time the pH of the reaction mixture was adjusted to 6.5–7 with 0.1M sodium hydroxide, and the solution was concentrated under reduced pressure to about 10 ml. The concentrate was dialyzed against distilled water and freeze-dried to yield 0.36 g of fragmented heparin preparation.

B. Conjugation of Heparin Fragments to IL-2.

RP-HPLC purified recombinant des-alanyl, ser$_{125}$ IL-2 (where the cysteine at position 125 is replaced by serine and the N-terminal alanyl residue is deleted), prepared as described in U.S. Pat. Nos. 4,518,584 and 4,530,787, supra, or the post-diafiltered des-ala$_1$, ser$_{125}$ IL-2 from the production process described hereinabove, was employed in this example.

To a solution of 2.0 mg IL-2 in 1 ml 0.1M sodium phosphate buffer, pH 7.5 with 0.1% SDS was added 5 mg of the heparin preparation and 2 mg NaCNBH$_3$. The solution was mixed thoroughly and kept overnight (16–18 hours) at 37° C..

C. Isolation of Modified IL-2.

The reaction mixture was applied to a Biogel P6DG column and eluted with 0.1M sodium phosphate buffer, pH 7.0 to remove SDS and NaCNBH$_3$ and unreacted IL-2. Analysis using a Dupont GF-250 sizing column showed a molecular weight of about 160,000. Aliquots of the fractions were assayed for IL-2 bioactivity (cell proliferation) by the methods generally described in Gillis, S., et al. *J. Immunol.*, 120, 2027–2032 (1978), the disclosure of which is incorporated herein by reference.

EXAMPLE II

Characterization of Heparinized IL-2

A. Bioactivity of Heparinized IL-2.

The fraction from the aforementioned HPLC column elutions of heparin-conjugated IL-2 was assayed by the IL-2 cell proliferation bioassay described in Example I.C. The specific activity of the conjugates was found to be about $4.8 \times 10^6$ units/mg.

B. Solubility of Heparinized IL-2 compared to Unmodified IL-2.

The solution of heparin IL-2 in 0.1M sodium phosphate pH 7 contained 0.3 mg/ml protein and was assayed for SDS content by acridine orange assay. The SDS concentration was about 60 $\mu$g/mg protein. Unmodified IL-2 was not soluble in this buffer at that low SDS concentration, but the solution of conjugate remained clear on standing at 4° C. for several days.

In summary, the present invention is seen to provide a pharmaceutical composition wherein a biologically active specific protein selectively conjugated to a heparin fragment and thereby made soluble or more soluble in an aqueous medium at physiological pH is dissolved in such medium. The conjugation serves to solubilize the normally hydrophobic, poorly water-soluble protein in water at pH 6–8, and to retain its biological activity. Without the conjugation, the protein must be solubilized by addition of solubilizing agents such as detergents or denaturants, by raising the pH in combination with addition of a stabilizer or by lowering the pH.

Various modifications of the above-described modes for carrying out the invention which are obvious to those skilled in the field of pharmaceutical formulation or related fields are intended to be within the scope of the following claims.

What is claimed is:

1. A pharmaceutical composition comprising a nontoxic, inert, pharmaceutically acceptable aqueous carrier medium in which is dissolved a biologically active, selectively conjugated, recombinant protein selected from the group consisting of $\beta$-interferon, interleukin-2, and an immunotoxin, wherein the protein is covalently conjugated via at least one of its lysine residues to at least one heparin fragment having a terminal 2,5-anhydro-D-mannose residue through the aldehyde group of such residue, wherein said protein in its unconjugated form is normally hydrophobic and poorly soluble in said aqueous carrier medium at pH 6–8 in the absence of a solubilizing agent.

2. The composition of claim 1 wherein the medium is at a pH of about 5–8 and contains a buffer.

3. The composition of claim 1 wherein the medium is at a pH of about 6.5–7.8 and contains a buffer.

4. The composition of claim 1 wherein the protein is a recombinant protein from a human source.

5. The composition of claim 4 wherein said protein has the amino acid which is at position 104 or 125 on those at both position in the native protein substituted with a neutral amino acid.

6. The composition of claim 5 wherein said IL-2 protein is ser$_{125}$ IL-2, des-ala$_1$Il-2, des-ala$_1$ser$_{125}$ IL-2, des-ala$_1$ala$_{104}$IL-2, or des-ala$_1$ala$_{104}$ser$_{125}$ IL-2.

7. The composition of claim 4 wherein said $\beta$-IFN protein has the cysteine residue at position 17 in the native protein substituted with a neutral amino acid.

8. The composition of claim 7 wherein said $\beta$-IFN protein is ser$_{17}$ IFN-$\beta$.

9. The composition of claim 4 wherein said protein is an immunotoxin with recombinant ricin A chain.

10. A process for preparing a pharmaceutical composition comprising:

(a) preparing a heparin fragment having a terminal 2,5-anhydro-D-mannose residue with an aldehyde not involved in intramolecular hemiacetal formation;

(b) reacting a biologically active, normally hydrophobic, poorly water-soluble recombinant protein selected from the group consisting of β-interferon, interleukin-2, and an immunotoxin with said aldehyde of said heparin fragment so as to provide a more water-soluble, biologically active, selectively conjugated recombinant protein; and (c) formulating said protein in a non-toxic, inert, pharmaceutically acceptable aqueous carrier medium.

11. The process of claim 10 wherein step (a) is carried out by treating the sodium salt of heparin with nitrous acid.

12. The process of claim 10 wherein step (b) is carried out by reductive amination.

13. The process of claim 12 wherein the reaction is carried out using $NaCNBH_3$.

14. The process of claim 10 wherein step (c) is carried out at pH 6–8.

15. The process of claim 10 wherein said protein is recombinant and from a human source.

16. The process of claim 15 wherein said protein is interleukin-2.

* * * * *